US011464889B2

(12) United States Patent
Ou et al.

(10) Patent No.: US 11,464,889 B2
(45) Date of Patent: Oct. 11, 2022

(54) ANTIMICROBIAL-CONTAINING SILICONE LUBRICIOUS COATINGS

(71) Applicant: Ethicon, Inc., Somerville, NJ (US)

(72) Inventors: Duan Li Ou, Warren, NJ (US); Frank R. Cichocki, Jr., Easton, PA (US)

(73) Assignee: Ethicon, Inc., Raritan, NJ (US)

( * ) Notice: Subject to any disclaimer, the term of this patent is extended or adjusted under 35 U.S.C. 154(b) by 252 days.

(21) Appl. No.: 16/697,223

(22) Filed: Nov. 27, 2019

(65) Prior Publication Data
US 2020/0172740 A1 Jun. 4, 2020

Related U.S. Application Data

(60) Provisional application No. 62/773,102, filed on Nov. 29, 2018.

(51) Int. Cl.
*A61L 27/54* (2006.01)
*A61L 2/03* (2006.01)
(Continued)

(52) U.S. Cl.
CPC ............... *A61L 27/54* (2013.01); *A61L 2/03* (2013.01); *A61L 2/07* (2013.01); *A61L 2/20* (2013.01); *A61L 2/26* (2013.01); *A61L 17/005* (2013.01); *A61L 17/145* (2013.01); *A61L 31/10* (2013.01); *A61L 31/14* (2013.01); *A61L 31/16* (2013.01); *B05B 7/1606* (2013.01); *B05B 7/1686* (2013.01); *B05B 12/081* (2013.01); *B05B 15/00* (2013.01); *B05B 17/0615* (2013.01); *B05D 1/02* (2013.01); *B05D 3/0493* (2013.01); *C09D 5/14* (2013.01); *C09D 7/20* (2018.01); *C09D 7/62* (2018.01); *C09D 183/04* (2013.01); *C10M 107/50* (2013.01); *A61L 2202/181* (2013.01);
(Continued)

(58) Field of Classification Search
None
See application file for complete search history.

(56) References Cited

U.S. PATENT DOCUMENTS 2,941,696 A 6/1960 Edwin
3,187,752 A * 6/1965 Glick .................... A61L 17/145
606/231
(Continued)

FOREIGN PATENT DOCUMENTS

CN 104531056 A 4/2015
CN 105586001 A 5/2016
(Continued)

OTHER PUBLICATIONS

IP.com search of the PGPub (Year: 2021).*
(Continued)

*Primary Examiner* — Peter A Salamon

(57) ABSTRACT

Novel, lubricious antimicrobial coatings for medical devices are disclosed. The coatings provide improved lubricity and durability and are readily applied in coating processes at low temperatures that do not deform the device and preserves the antimicrobial effectiveness of the antimicrobial agent. The present invention is also directed to a novel platinum catalyst for use in such coatings. The catalyst provides for rapid curing, while inhibiting cross-linking at ambient temperatures, thereby improving the production pot life of the coatings.

22 Claims, 4 Drawing Sheets

(51) Int. Cl.
| | | |
|---|---|---|
| *A61L 2/07* | (2006.01) | |
| *A61L 2/20* | (2006.01) | |
| *A61L 2/26* | (2006.01) | |
| *A61L 17/00* | (2006.01) | |
| *B05B 7/16* | (2006.01) | |
| *B05B 15/00* | (2018.01) | |
| *A61L 17/14* | (2006.01) | |
| *C09D 7/20* | (2018.01) | |
| *C09D 7/62* | (2018.01) | |
| *A61L 31/10* | (2006.01) | |
| *A61L 31/14* | (2006.01) | |
| *A61L 31/16* | (2006.01) | |
| *C09D 5/14* | (2006.01) | |
| *C09D 183/04* | (2006.01) | |
| *C10M 107/50* | (2006.01) | |
| *B05B 12/08* | (2006.01) | |
| *B05B 17/06* | (2006.01) | |
| *B05D 1/02* | (2006.01) | |
| *B05D 3/04* | (2006.01) | |
| *C10N 40/00* | (2006.01) | |
| *C10N 30/16* | (2006.01) | |
| *C10N 50/08* | (2006.01) | |
| *A61M 11/00* | (2006.01) | |

(52) U.S. Cl.
CPC ... *A61L 2202/182* (2013.01); *A61L 2300/202* (2013.01); *A61L 2300/404* (2013.01); *A61L 2300/606* (2013.01); *A61L 2400/10* (2013.01); *A61L 2420/02* (2013.01); *A61L 2420/04* (2013.01); *A61L 2420/06* (2013.01); *A61M 11/005* (2013.01); *C10M 2229/0445* (2013.01); *C10N 2030/16* (2013.01); *C10N 2040/50* (2020.05); *C10N 2050/08* (2013.01)

(56) References Cited

U.S. PATENT DOCUMENTS

| | | | |
|---|---|---|---|
| 3,445,420 A | 5/1969 | Kookootsedes et al. | |
| 3,490,651 A | 1/1970 | Abplanalp | |
| 3,675,821 A | 7/1972 | Morane et al. | |
| 3,775,452 A | 11/1973 | Karstedt | |
| 3,814,730 A | 6/1974 | Karstedt | |
| 4,234,108 A | 11/1980 | Diamond | |
| 4,340,155 A | 7/1982 | Obrist | |
| 4,791,149 A | 12/1988 | Pocknell | |
| 5,020,694 A | 6/1991 | Pettengill | |
| 5,026,768 A | 6/1991 | Liles | |
| 5,211,316 A | 5/1993 | Adalberto et al. | |
| 5,431,303 A | 7/1995 | Miskell | |
| 5,447,987 A | 9/1995 | Sato et al. | |
| 5,577,637 A | 11/1996 | Voss | |
| 5,647,510 A | 7/1997 | Keller | |
| 5,776,268 A | 7/1998 | Mcjames et al. | |
| 5,780,543 A | 7/1998 | Adachi et al. | |
| 6,265,480 B1 | 7/2001 | Enami et al. | |
| 6,537,246 B1 | 3/2003 | Unger et al. | |
| 6,613,185 B1 | 9/2003 | Valade et al. | |
| 6,951,654 B2* | 10/2005 | Malcolm | A61P 31/00 424/430 |
| 7,393,547 B2* | 7/2008 | Nelson | A61F 2/203 424/486 |
| 7,481,333 B2 | 1/2009 | Goldberg et al. | |
| 7,798,366 B2 | 9/2010 | Hoshino | |
| 8,021,650 B2 | 9/2011 | Tamareselvy et al. | |
| 8,357,147 B2 | 1/2013 | Burkinshaw et al. | |
| 8,596,499 B2 | 12/2013 | Vogt et al. | |
| 8,728,599 B2 | 5/2014 | Fang et al. | |
| 8,969,910 B2 | 3/2015 | Katayama | |
| 9,038,858 B2 | 5/2015 | Hanai et al. | |
| 9,180,476 B2 | 11/2015 | Werner et al. | |
| 9,302,282 B2 | 4/2016 | Bertin et al. | |
| 9,408,971 B2 | 8/2016 | Carlyon | |
| 9,422,404 B2 | 8/2016 | Curtis et al. | |
| 9,434,857 B2 | 9/2016 | Ou | |
| 9,511,034 B1 | 12/2016 | Garrett | |
| 9,642,949 B2* | 5/2017 | Hai | A61L 33/0011 |
| 9,649,650 B2 | 5/2017 | Werner et al. | |
| 9,655,917 B2* | 5/2017 | Hai | A61L 31/10 |
| 9,764,099 B2 | 9/2017 | Rimsa et al. | |
| 10,219,793 B2 | 3/2019 | Quintero et al. | |
| 10,441,947 B2 | 10/2019 | Ou | |
| 2001/0011162 A1 | 8/2001 | Epstein | |
| 2001/0019721 A1 | 9/2001 | Brandt et al. | |
| 2002/0076260 A1 | 6/2002 | Heusser | |
| 2002/0193879 A1* | 12/2002 | Seder | A61F 2/203 623/9 |
| 2003/0044451 A1* | 3/2003 | McGhee | A61L 29/085 424/443 |
| 2003/0077316 A1 | 4/2003 | Nichols et al. | |
| 2003/0082223 A1 | 5/2003 | Healy et al. | |
| 2003/0183651 A1 | 10/2003 | Greer | |
| 2004/0004088 A1 | 1/2004 | Yerby et al. | |
| 2004/0181943 A1* | 9/2004 | Kwiecien | B26B 21/443 30/41 |
| 2005/0020844 A1* | 1/2005 | Nelson | C08G 77/04 556/467 |
| 2005/0029296 A1 | 2/2005 | Hansen et al. | |
| 2005/0048124 A1* | 3/2005 | Sarangapani | A61K 33/38 424/486 |
| 2005/0127119 A1 | 6/2005 | Keller | |
| 2005/0182443 A1 | 8/2005 | Jonn et al. | |
| 2005/0256573 A1* | 11/2005 | Seder | A61F 2/203 623/9 |
| 2006/0009099 A1* | 1/2006 | Jonn | A61L 15/58 442/43 |
| 2006/0134313 A1* | 6/2006 | Guggenbichler | A61L 29/06 427/2.1 |
| 2007/0043332 A1* | 2/2007 | Malcolm | A61K 9/0036 604/500 |
| 2007/0104665 A1 | 5/2007 | Jones et al. | |
| 2007/0293820 A1 | 12/2007 | Dacquay et al. | |
| 2008/0054020 A1 | 3/2008 | Pierson et al. | |
| 2008/0275403 A1 | 11/2008 | Maaskamp et al. | |
| 2009/0004246 A1* | 1/2009 | Woolfson | A61K 31/00 424/430 |
| 2009/0026660 A1* | 1/2009 | Nelson | A61L 27/54 264/331.13 |
| 2009/0076480 A1* | 3/2009 | Pudleiner | A61L 29/06 604/508 |
| 2009/0108021 A1 | 4/2009 | Hansen et al. | |
| 2010/0280547 A1 | 11/2010 | D'Alessio et al. | |
| 2010/0330025 A1* | 12/2010 | Messersmith | A61L 27/50 424/78.17 |
| 2011/0027753 A1 | 2/2011 | Maurat et al. | |
| 2011/0091669 A1* | 4/2011 | Tang | C08J 7/043 428/34.1 |
| 2011/0143148 A1 | 6/2011 | Butts et al. | |
| 2011/0272433 A1 | 11/2011 | Vogt et al. | |
| 2012/0237461 A1 | 9/2012 | Yu et al. | |
| 2012/0328787 A1 | 12/2012 | Marrot et al. | |
| 2013/0004586 A1* | 1/2013 | Vachon | B01J 41/07 424/618 |
| 2013/0059109 A1 | 3/2013 | Kretschmann et al. | |
| 2013/0122314 A1 | 5/2013 | Ou | |
| 2013/0123720 A1 | 5/2013 | Lind et al. | |
| 2013/0150828 A1* | 6/2013 | Conway | A61L 29/085 604/544 |
| 2013/0171265 A1 | 7/2013 | Saxena | A61K 8/899 424/618 |
| 2013/0310780 A1* | 11/2013 | Phillips | A61L 15/26 604/319 |
| 2013/0310781 A1* | 11/2013 | Phillips | C08L 83/04 604/319 |
| 2014/0221522 A1* | 8/2014 | Antoni | A61L 31/10 523/105 |
| 2015/0159066 A1* | 6/2015 | Hartwell | A61M 1/90 604/319 |
| 2016/0120706 A1 | 5/2016 | Collinson et al. | |

(56) References Cited

U.S. PATENT DOCUMENTS

| | | | |
|---|---|---|---|
| 2016/0220497 A1* | 8/2016 | Caprasse | A61K 8/895 |
| 2016/0354172 A1* | 12/2016 | Krogman | C08J 7/056 |
| 2017/0224823 A1* | 8/2017 | Blanda | A61K 31/565 |
| 2018/0030327 A1 | 2/2018 | Zhang et al. | |
| 2018/0163090 A1 | 6/2018 | Ou | |
| 2018/0338945 A1* | 11/2018 | Sambasivam | A61P 31/04 |
| 2019/0001019 A1 | 1/2019 | Lindgren et al. | |
| 2020/0172740 A1* | 6/2020 | Ou | B05D 3/0493 |
| 2021/0369258 A1 | 12/2021 | Ou et al. | |
| 2021/0369276 A1 | 12/2021 | Ou et al. | |
| 2021/0369639 A1 | 12/2021 | Ou | |
| 2021/0371190 A1 | 12/2021 | Ou et al. | |
| 2021/0371596 A1 | 12/2021 | Ou et al. | |
| 2021/0371658 A1 | 12/2021 | Ou | |
| 2021/0371662 A1 | 12/2021 | Ou | |

FOREIGN PATENT DOCUMENTS

| | | |
|---|---|---|
| CN | 106009688 A | 10/2016 |
| EP | 3388037 A1 | 10/2018 |
| JP | 11349897 A | 12/1999 |
| KR | 0039498 A | 4/2016 |
| WO | 9725085 | 7/1997 |
| WO | 2010/128855 A2 | 11/2010 |
| WO | 2013/074732 A1 | 5/2013 |
| WO | 2016094084 A1 | 6/2016 |
| WO | 2017158340 A1 | 9/2017 |

OTHER PUBLICATIONS

Google scholar keyword search (Year: 2021).*
International Search Report dated Aug. 13, 2021 for International Application No. PCT/IB2021/054533.
International Search Report dated Aug. 18, 2021 for International Application No. PCT/IB2021/054531.
International Search Report dated Feb. 21, 2020 for International Application No. PCT/IB2019/060233.
International Search Report dated Feb. 21, 2020 for International Application No. PCT/IB2019/060235.
International Search Report dated Jan. 11, 2022 for International Application No. PCT/IB2021/054534.
International Search Report dated Jul. 29, 2021 for International Application No. PCT/IB2021/054515.
International Search Report dated Jul. 30, 2021 for International Application No. PCT/IB2021/054518.
Lewis, et al ., The chemistry of fumarate and maleate inhibitors with platinum hydrosilylation catalysts, Journal of Organometallic Chemistry, 1996, pp. 221-227, vol. 521 Issue 1.

* cited by examiner

ANTIMICROBIAL-CONTAINING SILICONE LUBRICIOUS COATINGS

CROSS-REFERENCE TO RELATED APPLICATION(S)

This application claims the benefit of U.S. Provisional Application No. 62/773,102 filed Nov. 29, 2018, the contents of which is incorporated herein by reference in its entirety for all purposes.

This application is related to U.S. Non-Provisional application Ser. No. 16/697,222, being filed concurrently herewith and having a common assignee, the contents of each are herein incorporated by reference in their entirety for all purposes.

TECHNICAL FIELD

The field of art to which this invention pertains is antimicrobial-containing silicone-based lubricious coatings, in particular, silicone-based lubricious coatings for use on medical devices that include an antimicrobial agent.

BACKGROUND OF THE INVENTION

Lubricious coatings are typically required for implantable or insertable medical devices such as sutures, hypodermic needles, surgical needles, catheters, and cutting devices that contact tissue. The primary purpose of such coatings is to ease the penetration or insertion of the device into and through tissue, thereby facilitating a procedure.

A number of conventional, biocompatible lubricants have been developed for such applications, and they are typically silicone (e.g., polydimethylsiloxane) or silicone-containing coatings. For example, condensation-cured silicone coatings are known to be useful as lubricious coatings on medical devices. Such coating formulations contain amino and alkoxyl functional groups, which can be cured (cross-linked) at relatively low temperatures and high humidity levels. It is also known to use an aminopropyl-containing silicone as a lubricious coating for syringe needles. Those coatings use an epoxy-containing silicone as a cross-linking agent and may have improved penetration performance with multiple penetrations. It is also known to utilize thermoplastic polymers such as polypropylene (e.g., in powder form) in blends of silicone solutions to improve the mechanical properties of the resulting coating layers. The polypropylene powders may increase the durability of silicone needle coatings without sacrificing lubricity. Most of the known and conventionally used silicone coatings listed above require a lengthy thermal curing step after application, which is quite often unsuitable for rapid, high speed production processes.

Attempts have been made to improve coating cure times including rapid UV curable silicone lubricious coatings that can be cured rapidly (<10 seconds) on a medical device, such as needle, after UV light exposure. However, the potential hazard of certain UV curable components typically contained in such coatings may provide cause for concern.

Karstedt of GE Silicone invented a highly active platinum catalyst for hydrosilylation at the beginning of the 1970's (U.S. Pat. No. 3,775,452). The "Karstedt catalyst" is highly active at ambient temperature, and this quality makes it difficult to use in most commercial silicone coatings without the addition of an inhibitor. Several other platinum catalysts had been subsequently invented attempting to address this problem. For example, platinum-cyclovinylmethylsiloxane complex was made immediately after the invention of the Karstedt catalyst (U.S. Pat. No. 3,814,730), and this catalyst is purported to provide longer production process pot life for a vinyl/hydride reactive coating solution mixture. Each of those catalysts is still commonly used in the silicone coating industry.

Commonly assigned U.S. Pat. Nos. 9,434,857 and 10,441,947 describe novel, lubricious coatings for medical devices. The coatings provide improved lubricity and durability and are readily applied in conventional coating processes. These patents are also directed to a novel platinum catalyst for use in such coatings. The catalyst provides for rapid curing, while inhibiting cross-linking at ambient temperatures, thereby improving the production pot life of the coatings. A limitation of such compositions is that they are not suitable for coating of polymeric materials that would be deformed or affect the effectiveness of an antimicrobial agent used in the coating composition due to the elevated temperatures (e.g., above 160 C) required for the compositions to be cured to form coatings.

In order to be useful on medical devices such as surgical needles and sutures, it is critical that lubricious silicone coatings be durable and easy to apply in a uniform, consistent manner. A surgical procedure in which tissue is approximated or closed with surgical sutures typically requires multiple passes of the surgical needle and suture through tissue. Ease of penetration over multiple passes through tissue will make the surgeon's job easier and this will likely result in a better tissue repair or closure. The patient will benefit not only by enhanced healing and superior outcome, but also by a faster procedure resulting in a shorter time for possible exposure of the wound or opening to pathogens in the environment, and also requiring a shorter period of time that the patient is under general anesthesia, when anesthesia is required.

Some medical devices such as surgical needles are typically manufactured in high speed production processes. For example, U.S. Pat. No. 5,776,268, incorporated by reference, discloses such processes. After the needles are formed and shaped (typically from wire stock), the in-process needles are cleaned, and the needles are coated with lubricious coatings in a conventional manner such as by dipping, spraying, brushing, etc. After application of the coatings in a uniform manner to substantially coat the exterior surfaces of the needles, the needles are then moved into appropriate curing equipment, such as an oven, for a coating curing process wherein energy (e.g., thermal) is provided to cure the silicone coatings.

Silicone coatings are typically prepared at the manufacturing site by mixing the silicone polymer components with a suitable catalyst and solvents. Such coatings and catalysts, especially when of medical grade for use on medical devices, are expensive and typically have what is conventionally known in this art as a short "pot life". The term pot life, as conventionally used in the art, has the meaning that the silicone coatings when mixed with catalyst and ready for application in a coating process typically have a limited amount of time in which they are useful because of cross-linking that occurs at ambient conditions in the production facility. Such short pot life can result in a number of known problems, including for example, premature curing, leading to a viscosity increment of the coating solution during the time of its usage. This will typically cause inconsistencies in the resulting coating on the surface of the medical device, resulting in both visual and performance deficiencies.

There is a need in this art for improved silicone coatings for medical devices that have improved lubricity and durability for multiple passes through tissue. There is also a need for improved catalytic compositions and silicone coatings that have improved cure times without sacrificing lubricity and durability, which do not contain potentially harmful ingredients and are capable of being applied under conditions that do not deform the device to be coated such as sutures and other polymeric devices and which preserve the antimicrobial activity of the antimicrobial agents.

There is a further need in the art for improved catalysts for silicone coatings that provide for rapid curing when exposed to heat but which are relatively stable in a silicone coating solution over time at ambient conditions and for extended periods of time in typical production environments.

There is also a need to deliver antimicrobial agents onto medical device such as sutures to prevent surgical site infection. A different carrier for antimicrobial agent is proposed in this invention disclosure as the vehicle to deliver triclosan onto medical devices.

The current standard of care involves coating or impregnating the suture with triclosan. While incorporating triclosan into the suture is highly advantageous, there are some process challenge that are needed to be addressed. Firstly, some sutures are not easily coated with triclosan and do not absorb triclosan readily. Various suture coatings can be utilized to then incorporate triclosan in these coatings. Uniform applications of such coatings to sutures can be technically challenging.

Secondly, triclosan needs to be released from non-absorbable sutures with some delay, while silicone is good candidate for the controlled release There is a need to deliver antimicrobial agents onto wide range of medical devices other than suture and silicone is a good candidate as the vehicle to these agents due to its versatility and its ability to be converted into many different sizes and shapes. Some examples of these medical devices include and are not limited to Blake® drains, stainless steel sutures, orthopedic screws and pins, etc. Triclosan is difficult to be absorbed into the non-absorbable surface of these medical devices.

The proposed silicone materials of this invention cross link at relatively low temperatures (70 to 110 C). Under such a mild curing conditions, active antimicrobial components such as triclosan remains in the matrix of silicone and does not decompose or evaporate.

A range of medical devices have been coated with triclosan-containing silicone compositions of this invention and the antimicrobial effect of the resulting coated devices were evaluated, which show a zone of inhibition against selected bacteria around the treated devices.

SUMMARY OF THE INVENTION

Accordingly, novel compositions and lubricious silicone coating compositions are disclosed.

In one embodiment, the coating compositions contain a first cross-linkable silicone polymer having reactive functionalities, a siloxane cross-linking agent, and an antimicrobial agent. In instances where sutures are coated, a silica-containing composition with may be added as a separate component, but more preferably the silica is contained in the cross-linkable silicone polymer. The coating compositions may also contain a platinum catalyst.

Another aspect of the present invention is a medical device having a surface, wherein at least part of the surface is coated with the above-described novel silicone coating composition.

Yet another aspect of the present invention is a method of coating a medical device with a silicone, lubricious coating composition. In the novel method of coating the medical device, a medical device is provided having a surface. A lubricious silicone coating is applied to at least part of the surface. The coating composition contains a cross-linkable silicone polymer and in the case of a suture or for a reservoir for triclosan, a silica-containing composition which may be added as a separate component, but more preferably the silica component is contained in the cross-linkable silicone polymer. The coatings also contain a silicone cross-linking agent and a catalyst. In certain embodiments, coating solutions do not contain a silica-containing composition such as for coating compositions for coating medical devices containing a metallic component or for silicone drains, and in these embodiments, a non-cross-linkable silicone polymer is preferably added into the cross-linkable silicone polymer.

Still yet another aspect of the present invention is a novel platinum catalyst for use with cross-likable silicone coatings containing an antimicrobial agent. The catalyst consists of a platinum complex having the following formula:

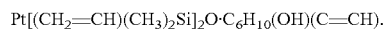

$$Pt[(CH_2=CH)(CH_3)_2Si]_2O \cdot C_6H_{10}(OH)(C=CH).$$

A further aspect of the present invention is a method of curing a cross-linkable silicone polymer containing coating solution using the above-described catalyst.

These and other aspects and advantages of the present invention will become more apparent from the following description.

BRIEF DESCRIPTION OF THE DRAWINGS

FIG. 3 is a depiction of the heating profile for Example 6a.

DETAILED DESCRIPTION OF THE INVENTION

Figure 1:
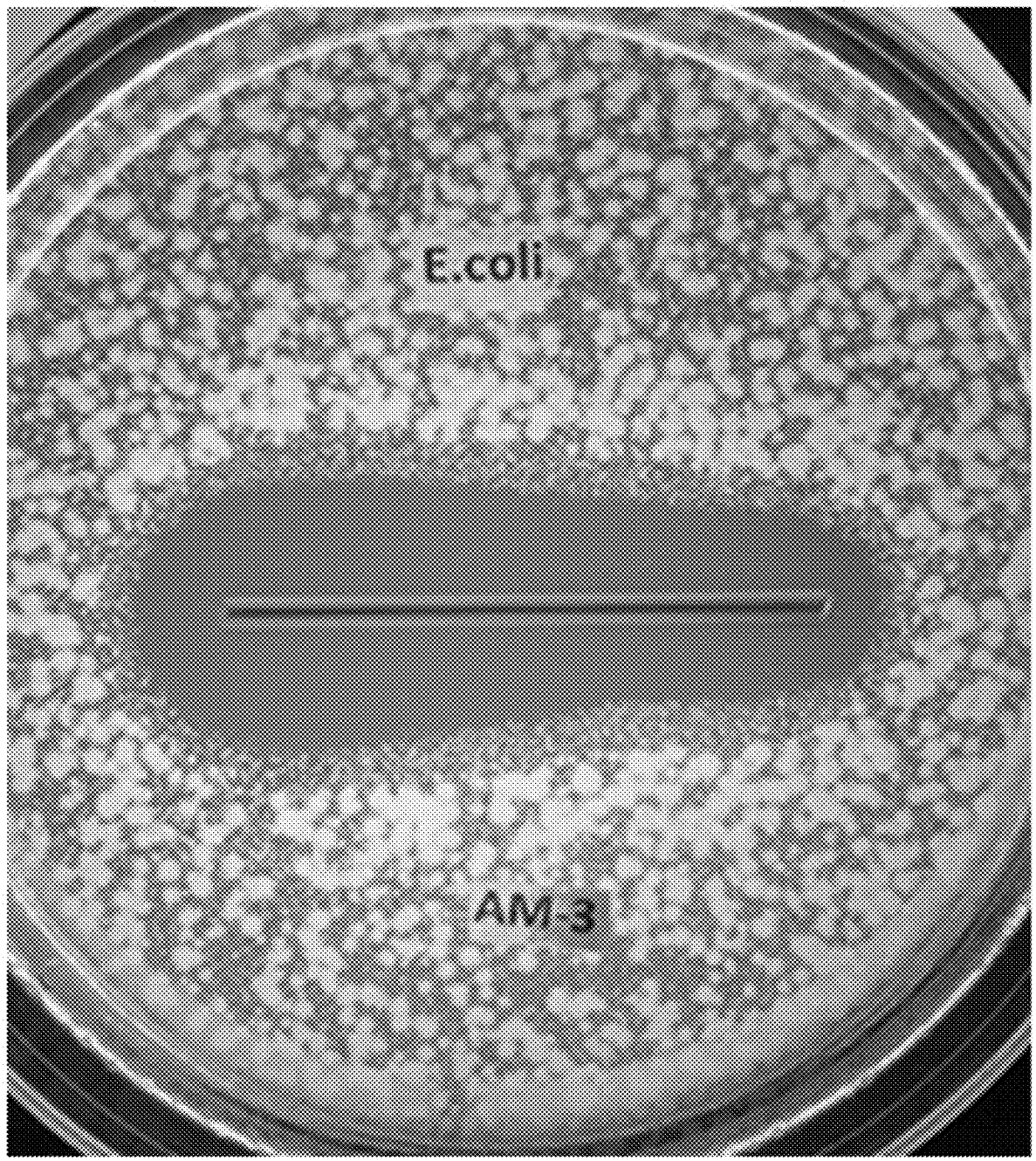
FIG. 1 is a Zone of Inhibition photo for one of the test articles coated with one embodiment of novel antimicrobial coatings of this invention.

The terms silicone and siloxane are conventionally used interchangeably in this art, and that usage has been adopted herein. Furthermore, as used herein, the term "ambient temperature(s)" is intended to describe temperatures from about 20 to about 25 C.

Lubricious Coating Compositions One aspect of the present invention is directed to novel lubricious silicone coating compositions which are particularly useful for coating surfaces of medical devices such as surgical needles and sutures and other polymeric medical devices.

In one embodiment, the compositions include a mixture of a cross-linkable siloxane polymer and an antimicrobial agent a conventional silicone cross-linking agent, and a platinum catalyst. The silicone polymer components are blended with conventional aromatic organic solvents, including, for example, xylene and aliphatic organic solvents (such as, for example, hexane or its commercial derivatives) to form coating solutions or compositions. Other suitable solvents for coating solutions include but are not limited to low molecular weight siloxane, e.g., hexamethyldisiloxane.

The cross-linkable siloxane polymers useful in the coating compositions of the present invention will have reactive functionalities or terminal functional groups, including but not limited to vinyl terminated, hydroxyl and acrylate functional groups. The cross-linkable siloxane polymers that can be used in the lubricious coatings of the present invention preferably include vinyl terminated polydialkylsiloxane or vinyl terminated polyalkoarylsiloxane. Examples include but are not limited to the following vinyl terminated siloxane polymers: polydimethyl siloxane, polydiphenylsilane-dimethylsiloxane copolymer, polyphenylmethylsiloxane, polyfluoropropylmethyl-dimethylsiloxane copolymer and polydiethyl siloxane. It is particularly preferred to use vinyl terminated cross-linkable polymethyl siloxane.

The cross-linking agents that can be used in the coatings of the present invention include conventional silicone cross-linking agents such as, for example, polymethylhydrosiloxane, polymethylhydro-co-polydimethylsiloxane, polyethyhydrosiloxane, polymethylhydrosiloxane-co-octylmethylsiloxane, polymethylhydrosiloxane-co-methylphenylsiloxane. One preferred conventional catalyst for use in the coatings of the present invention is polymethylhydrosiloxane. Precise control of cross-link density in the coatings of the present invention is achieved by precise control of the ratio of non-cross-linkable silicone polymer (e.g., polydimethylsiloxane) to fully cross-linked polymer. The fully cross-linked polymer is formed by a reaction between the functionalized cross-linkable polymer and the cross-linking agent, for example, a vinylsilylation reaction between vinyl-terminated polydimethylsiloxane and polymethylhydrosiloxane optionally in the presence of a platinum complex catalyst. The ratio between non-cross-linkable polymer, e.g., polydimethylsiloxane, and fully cross-linked polymer is sufficiently effective to provide structural reinforcement to the resulting interpenetrating polymer networks, and is typically between about 0.1 wt./wt. and about 9 wt./wt., preferably between about 0.43 wt./wt. and about 2.33 wt./wt. The vinyl-terminated cross-linkable base polymer, e.g., polydimethylsiloxane base polymer, useful in the coatings of the present invention will have a molecular weight (Mw) of between about 10,000 and about 500,000 and preferably between about 50,000 to about 250,000. Examples of this polymer include but are not limited to: Gelest Product Code No. DMS-V51, DMS-V52, DMS-V61, DMS-V71, etc., available from Gelest, Inc., Morrisville, Pa. 19067. The typical molecular structure of vinyl terminated polydimethyldisiloxane is the following:

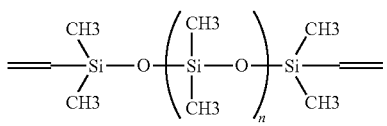

wherein n is defined by the molecular weight.

The molecular weights of the silicone polymers used herein can be estimated based on the relationship between viscosity and molecular weight (page 11, SILICONE FLUIDS: STABLE, INERT MEDIA ENGINEERING AND DESIGN PROPERTIES, Catalog published by Gelest, Inc. 11 East Steel Rd. Morrisville, Pa. 19067). Using A. J. Barry's relationship for molecular weights (M)>2,500 correlating the kinematic viscosity μ expressed in centistokes (cSt) at 25 C, the molecular weight M of silicones can be estimated as follows:

$$\log \mu_{cSt} = 1.00 + 0.0123 M^{0.5}$$

(as published by A. J. Barry in the *Journal of Applied Physics* 17, 1020 (1946)).

The cross-linkable siloxane polymer forms the matrix phase of the coating on surface or surfaces of a medical device. Vinyl terminated polydimethylsiloxane reacts with polymethylhydrosiloxane cross-linker in the presence of platinum catalyst under appropriate conditions; the vinyl terminated polydimethylsiloxane linear polymers are fully cross-linked to each other as the result of this reaction. The amount of polymethylhydrosiloxane cross-linker is in large stoichiometric excess compared to vinyl terminated polydimethylsiloxane base polymer. It is believed that the extra SiH functions in the cross-linker react with the OH functions on the surface of the medical devices, e.g., polymeric sutures, to form Si—O—C bonds at elevated temperature or in the case of steel needles, to form Si—O—Fe bonds. Covalent bonds thus created between the silicone coating and the device, as the result of this reaction, result in the adhesive attachment of the coating to the device's surface.

The polymethylhydrosiloxane cross-linkers, or cross-linking agents, used in the practice of the present invention will have a molecular weight (Mw) from about 1000 and about 3000, and preferably between about 1400 and about 2100.

An example of this polymer cross-linker includes, but is not limited to, Gelest Product Code No. HMS-991, HMS-992, available from Gelest, Inc., Morrisville, Pa. 19607. The typical molecular structure of the polymethylhydrosiloxane cross-linker is the following:

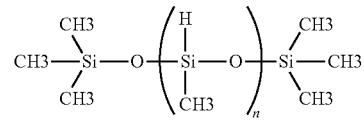

wherein n is defined by the molecular weight.

Polymethylhydro-co-polydimethylsiloxane can also be used as cross-linker or cross-linking agent in the novel coatings of the present invention. Examples of this polymer include, but are not limited to, Gelest Product Code No. HMS-301, HMS-501. The molecular weight of this siloxane polymer cross-linking agent will typically be from about 900 and about 5,000, and preferably about 1,200 to about 3,000. The typical molecular structure of polymethylhydro-co-polydimethylsiloxane cross linker is the following:

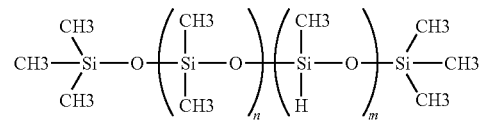

wherein n and m are defined by the molecular weight.

The non-cross-linkable siloxane used in some embodiments of the lubricious coatings of the present invention is preferably trimethylsilyl-terminated polydimethylsiloxane, which is a linear high molecular weight polydimethylsiloxane polymer, and which contains no reactive functions. This polymer provides a non-cross-linked phase in the resulting silicone coating and is believed to disperse in the matrix phase made from the cross-linked cross-linkable siloxane. The weight average molecular weight of this polymer will typically be between about 260,000 to about 10,000,000, preferably between about 400,000 to about 700,000. Examples of this polymer include, but are not limited to: Gelest Product Code No. DMS-D-56, DMS-T62, DMS-T61, DMS-D72, etc. The typical molecular structure of the non-cross linkable siloxane polymer is illustrated below:

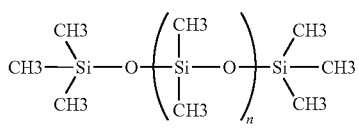

wherein n is defined by the molecular weight.

Silica-Containing Compositions

As used herein, the silica-containing compositions described for use with this invention include silica materials as a separate component (such as surface-treated silica) or from commercially available compositions that contain silica in a cross linkable silicone polymer mixture.

As a separate component, silica is incorporated into the coatings of this invention to improve its mechanical properties and create some form of friction to ensure knot security for the suture. Hexamethyl silyl surface treatment is needed for the silica filler to enable its compatibility to the polysiloxane polymer matrix which prevents phase separation in the coating solution. An example of treated silica includes hexamethyldisilazane treated silica i.e., trimethyl silyl surface treated silica filler (Gelest SIS6962.0).

In the case of silicone polymers already containing silica, these may be obtained from commercially available sources such as silica-containing composition selected from reactive silica-containing silicone bases including HCR (high consistent rubber) bases and LSR (liquid silicone rubber) bases, preferred are LSR bases. Other commercial examples of this material include and is not limited to Wacker 401-10, 401-20, 401-40 base; and a liquid silicone rubber base, a commercial example of this material includes and is not limited to Bluestar Silbione LSR 4370 base. These types of commercial silicone rubber bases are prepared by mixing a surface-treated silica filler with various molecular weights of vinyl terminated polydimethylsiloxane polymer. In-situ surface treatment may be performed during the mixing process to improve the compatibility between filler and polysiloxane polymer.

Antimicrobial Agents

Suitable antimicrobial agents can be those which can be homogenously distributed throughout the polymer matrix of the coating composition. For example, the antimicrobial agent can be any medicant having antibiotic or antimicrobial function, including chlorhexidine, polyhexamethylene biguanide (PHMB), octenidine, silver particles, triclosan, etc. In one form, particles of a material having high affinity for the antimicrobial agent can be distributed throughout the polymer matrix. For example, it is known that polycaprolactone and co-polymers based on polycaprolactone have a high affinity for triclosan. Thus, particles of (co)polymers of polycaprolactone can be included in the abradable coating when triclosan is selected as the antimicrobial agent. A preferred antimicrobial agent in use of this invention is triclosan. Preferably, the wt. % of triclosan in the coating composition is from about 1 to 40 wt. % (against total solids), more preferably from about 3 to about 30 wt. %, most preferably about 5 to 20 wt. %.

Catalyst

Bruce Karstedt of GE Silicone invented a highly active platinum catalyst (the "Karstedt catalyst") at the beginning of the 1970's (U.S. Pat. No. 3,775,452). Vinyl-terminated polydimethylsiloxane can react with a polymethylhydrosiloxane cross-linker in less than one minute at ambient temperature with as little as 10 ppm of the Karstedt catalyst. It is typically difficult or impossible to use this catalyst in conventional needle and suture manufacturing processes because of its high rate of catalytic activity, and since the economics of conventional production processes ideally and typically require up to a 8 hours pot life for the fully catalyzed silicone coating solution. The novel fast curing platinum catalyst of the present invention has been developed to address this issue, and the resulting mixtures of this novel catalyst together with the cross-linkable silicone polymers of the present invention, e.g., vinyl-terminated polydimethylsiloxane and polymethylhydrosiloxane, with silica fillers can be stable at ambient temperatures for more than about 8 hours. The cross-linking reaction between the cross-linkable silicone polymer and the cross-linking agent, for example, vinyl-terminated polydimethylsiloxane and polymethylhydrosiloxane, in the presence of the novel catalyst of the present invention can be switched on in less than 10 seconds at elevated temperature. The novel catalyst of the present invention is prepared by reacting the Karstedt catalyst with vinylcyclohexanol according to Scheme 1 as seen below. The novel catalyst of the present invention provides greater control over curing of the silicone coating solutions. This is conventionally referred to as "command cure".

Scheme 1

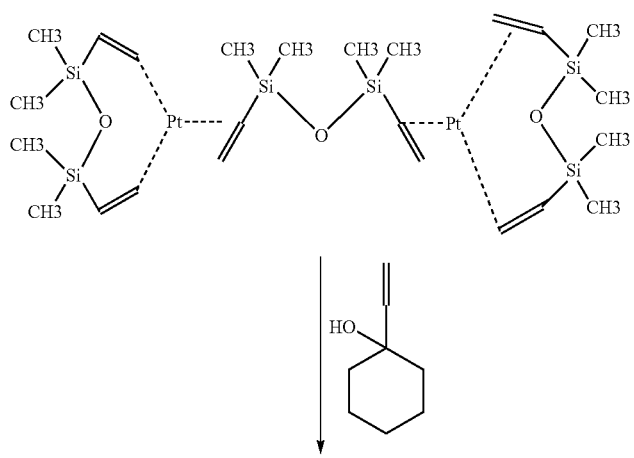

-continued

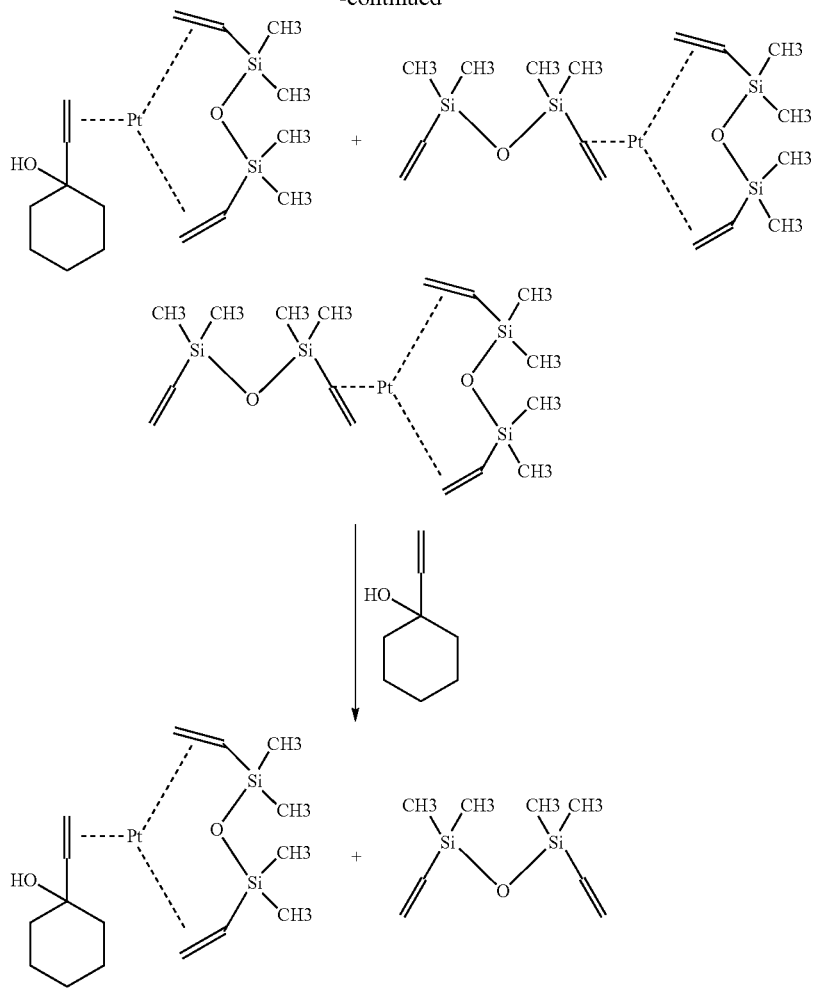

The catalyst of the present invention may be prepared in the following manner. Karstedt catalyst in xylene solution is mixed with vinylcyclohexanol at ambient temperature for a sufficiently effective time to complete the reaction, e.g., a half an hour, and completion of the reaction is indicated by a change of the color of the reaction mixture, from clear to brown.

The resulting catalyst was further diluted in tetramethyl disiloxane solution and ready to use in the preparation of the lubricious coating solutions of the present invention. The formula of the resulting platinum complex catalyst (platinum divinyltetramethyldisiloxane complex) is:

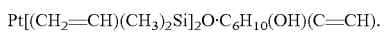

Pt[(CH$_2$=CH)(CH$_3$)$_2$Si]$_2$O·C$_6$H$_{10}$(OH)(C=CH).

It should be noted that the resulting catalyst reaction mixture will contain a small amount of the reaction product divinyltetramethyldisiloxane. This component does not affect the catalyst and is a low boiling point component that is rapidly boiled off. Accordingly, purification of the catalyst mixture to remove divinyltetramethyldisiloxane is optional, and it is believed that its presence will not affect the cross-linking reaction of a cross-linkable silicone polymer. The novel catalyst of the present invention is inhibited at low or ambient temperatures and activated at higher or curing temperatures, that is, the catalyst is inactivated at lower or ambient temperatures and activated at higher or curing temperatures. This allows for command cure (command cure catalytic action) of the cross-linkable components in silicone coatings to rapidly form coating films at desired curing temperatures and provides for long pot life and suitable for suture and other device coating process.

Solvent and Coating Mixing Procedure

The above silicone polymers and novel platinum catalyst are dispersed into low boiling point organic solvents to form the lubricious coating solution. Low temperature aliphatic solvents are used for the silicone dispersion. Aromatic solvents and tetramethyl disiloxane are commonly used for silicone dispersion. Typical examples include, but are not limited to, pentane, heptanes, hexane and their mixtures. The organic solvents are added at a concentration sufficient to allow effective blending of the silicone polymer components into a homogeneous coating solution. The total solvent concentration is from about 20 wt. % to 99 wt. %, depending upon the coating thickness requirement, and in this case the type of medical device. Those skilled in the art will appreciate that the coating thickness can be engineered by changing the solids content of the coating solution.

The sequence of the addition of components is important. The typical coating composition is prepared in the following manner. In the case when the silica is added as a separate component, the vinyl terminated polydimethylsiloxane is dispersed into the first solution such as hexamethyldisiloxane together with surface treated silica for up to two hours until fully homogeneous (solution 2). Heptane is then added (solution 3) and further mixing for one hour prior to the addition of polymethylhydrosiloxane cross linker. The solution is fully blended for one more hour after all of the catalyst is added as the final component.

In the following paragraph, the wt. % is the wt. % of total solids content in the coating solution. The novel coating compositions of the present invention will contain sufficient amounts of the polymeric components, silica-containing composition, cross-linking agent, catalyst, and solvent to effectively provide a silicone coating having high lubricity and durability, a long pot life, and suitable for application in conventional coating processes using conventional coating equipment.

The amount of organic solvent in the coating compositions of the present invention will typically be from about 20 wt. % to about 99.5 wt. %, depending on the type of medical devices which are coated. Those skilled in the art will appreciate that the amount of solvent present in the novel coating compositions of the present invention will vary with several factors, and that the solvent quantity in the coating compositions will be selected to engineer an efficacious coating. The factors typically considered include the method of application, the method of cure, the coating equipment utilized, ambient conditions, thickness, etc. It will be appreciated that each of the components of the coating compositions of the present invention may consist of blends of those components. For example, two or more different molecular weight non-cross-linkable silicone polymers may be used, or two or more cross-linkable silicone polymers having different functionalities and/or molecular weights may be used, surface treated silica filler etc.

There are three different types of embodiments of coating solutions described in the examples: one for metallic device and silicone drain, one for surgical suture and one for triclosan reservoir of operation room coating device.

For suture coating solution embodiments, the amount of the silica in the suture coating solution will be about 5 wt. % to about 40 wt. % (total solids), more typically about 10 wt. % to about 30 wt. % (total solids), and preferably about 15 wt. % to about 25 wt. % (total solids). The amount of the cross-linkable silicone polymer will typically be about 60 wt. % to about 95 wt. % (total solids), more typically about 70 wt. % to about 90 wt. % (total solids), and preferably about 75 wt. % to about 85 wt. % (total solids). The amount of the silicone cross-linking agent will typically be about 0.2 wt. % to about 6 wt. % (total solids), more typically about 1 wt. % to about 5 wt. % (total solids), and preferably about 2 wt. % to about 4 wt. % (total solids). The amount of the platinum catalyst based upon the total solids in the novel lubricious silicone coating compositions (platinum element in total solids) of the present invention will typically be about 0.0004 wt. % to about 0.0036 wt. %, more typically about 0.0012 wt. % to about 0.0028 wt. %, and preferably about 0.0016 wt. % to about 0.0024 wt. %.

For metallic device and silicone drain coating solution embodiments, the amount of non-cross linkable silicone polymer in the suture coating solution will be about 20 wt. % to about 80 wt. % (total solids), more typically about 30 wt. % to about 70 wt. % (total solids), and preferably about 40 wt. % to about 60 wt. % (total solids). The amount of the cross-linkable silicone polymer will typically be about 20 wt. % to about 80 wt. % (total solids), more typically about 30 wt. % to about 70 wt. % (total solids), and preferably about 40 wt. % to about 60 wt. % (total solids). The amount of the silicone cross-linking agent will typically be about 0.2 wt. % to about 6 wt. % (total solids), more typically about 1 wt. % to about 5 wt. % (total solids), and preferably about 2 wt. % to about 4 wt. % (total solids). The amount of the platinum catalyst based upon the total solids in the novel lubricious silicone coating compositions (platinum element in total solids) of the present invention will typically be about 0.0004 wt. % to about 0.0036 wt. %, more typically about 0.0012 wt. % to about 0.0028 wt. %, and preferably about 0.0016 wt. % to about 0.0024 wt. %.

For the coating solutions for a triclosan reservoir embodiments, the amount of the silica in the coating solution will be about 2.5 wt. % to about 20 wt. % (total solids), more typically about 5 wt. % to about 15 wt. % (total solids), and preferably about 7.5 wt. % to about 12.5 wt. % (total solids). The amount of the cross-linkable silicone polymer will typically be about 75 wt. % to about 99 wt. % (total solids), more typically about 80 wt. % to about 95 wt. % (total solids), and preferably about 85 wt. % to about 93 wt. % (total solids). The amount of the silicone cross-linking agent will typically be about 0.2 wt. % to about 6 wt. % (total solids), more typically about 1 wt. % to about 4 wt. % (total solids), and preferably about 1.5 wt. % to about 3 wt. % (total solids). The amount of the platinum catalyst based upon the total solids in the novel lubricious silicone coating compositions (platinum element in total solids) of the present invention will typically be about 0.00002 wt. % to about 0.0036 wt. %, more typically about 0.00003 wt. % to about 0.0020 wt. %, and preferably about 0.00004 wt. % to about 0.0010 wt. %.

The amount of organic solvent in the coating compositions of the present invention will typically be about 20 wt. % to about 99.5 wt. %, depending upon each type of medical device. Those skilled in the art will appreciate that the amount of solvent present in the novel coating compositions of the present invention will vary with several factors, and that the solvent quantity in the coating compositions will be selected to engineer an efficacious coating. The factors typically considered include the size and shape of the medical device, the material of the medical device, method of application, the method of cure, the coating equipment utilized, ambient conditions, thickness, etc. It will be appreciated that each of the components of the coating compositions of the present invention may consist of blends of those components. For example, two or more different molecular weight non-cross-linkable silicone polymers may be used, or two or more cross-linkable silicone polymers having different functionalities and/or molecular weights may be used, etc.

Coating Process

The novel silicone lubricious coating solutions of the present invention is applied to the surface of a medical device such as a polyester suture using conventional coating techniques and processes and conventional coating equipment. An example of coating equipment can be simple dip coating tanks and in-line convection oven for curing the coating. The coating can also be applied by a brushing, rolling, or spraying process. The vinyl silylation addition cross linking reaction can be completed in-line by passing through a drying oven. The curing time can be as short as 20 seconds at a temperature of 100 C, 120 seconds at 95 C or 60 minutes at 70 C. Flash cure can be achieved with the present lubricious silicone coating.

Due to the deformable nature of the polymeric medical devices at elevated temperatures and due to the low evaporation point of antimicrobial agents such as triclosan, it is desirable to not exceed treatment or coating temperatures above 120 C in the practice of this invention. Preferred coating treatment temperatures range from about 60-110 C, more preferably from about 90-100 C, and most preferably about 95 C.

Other conventional curing techniques which can be utilized with the novel silicone coating compositions of the present invention include thermal (e.g., convection heating), ultraviolet light, plasma, microwave radiation, electromagnetic coupling, ionizing radiation, laser, and the like. Prior to coating, the surfaces of the medical devices will be prepared in a conventional manner using conventional processes such as electro-polishing, oxidation, ultrasonic cleaning, plasma, corona discharge treatment, chemical cleaning, and the like.

Test Procedures for Coating Performance

As mentioned previously above, the medical devices that may be coated with the novel lubricious coatings include conventional medical devices such as surgical needles and sutures, hypodermic needles, catheters, surgical probes, endoscopes, syringes, scalpels, cutting blades, orthopaedic implants, trocars, cannulas, drains and the like. The medical devices will be constructed from conventional biocompatible materials including surgical stainless steels, titanium, PTFE, glass, alloyed steels, refractory metal alloys, memory alloys, silicone, polymers, composites comprising metallic and non-metallic components ingredients, combinations thereof, and the like. The biocompatible materials may include nonabsorbable materials and bioabsorbable materials.

Test Procedures

Zone of Inhibition (ZOI) Testing:

The triclosan containing silicone coated test article is placed into an agar medium that is inoculated with the test organism. Where the antimicrobial agent triclosan diffuses through the silicone carrier into the agar medium, and as long as the concentration of the antimicrobial agent is above the minimum inhibitory concentration (MIC), none of the susceptible organisms will grow on or around the disk for some distance. This distance is called a Zone of Inhibition. Assuming the antimicrobial agent has a diffusion rate in the medium, the presence of a Zone of Inhibition around a test article indicates that the organism is inhibited by the presence of the antimicrobial agent in the otherwise satisfactory growth medium. The diameter of the Zone of inhibition is inversely proportional to the MIC.

The triclosan containing silicone coated test articles were tested for antimicrobial properties utilizing this Zone of Inhibition test. Zone of Inhibition testing is a conventional method for estimating the inhibitory effects of antimicrobial substances against specific bacterial strains of interest. Zone of Inhibition assays are useful for testing diffusible agents. As the agent diffuses away from the disk, the concentration decreases logarithmically. The sensitivity of the organism to the agent is judged by the appearance and size of a Zone where no growth occurs, i.e., the Zone of Inhibition. Typically, a ZOI value of 3 mm is considered to be an effective zone to inhibit infection.

The triclosan-containing silicone coated test articles were aseptically placed in individual sterile Petri dishes and challenged with 100 micro liters of inoculum containing 10 colony-forming units (CFU) of *Staphylococcus aureus* or *Escherichia coli*. Trypticase soy agar (TSA) was poured into each dish and allowed to solidify. The plates were incubated at a temperature of 37 C for 48 hours. After incubation, the plates were examined under a darkfield colony counter and the Zones of Inhibition were measured.

EXAMPLES

The following examples are illustrative of the principles and practice of the present invention, although not limited thereto:

Example 1—Platinum Catalyst Synthesis Procedure 4 g of Gelest SIP 6831 (2.2% platinum divinyl tetramethyldisiloxane complex in xylene, Karstedt catalyst) was mixed with 4 g of vinylcyclohexanol xylene solution for 5 hours at ambient temperature and the mixture turns into dark brown color. The mixtures were diluted with 792 g tetramethyldisiloxane prior to its use.

Example 2a—Preparation of Coating Solution Leads to 20% Triclosan Containing Silicone This example provides triclosan containing silicone coating solution with a mixture of the components summarized in Table 2a.

TABLE 2a

| Coating Formulation | | |
|---|---|---|
| Component | Trade Name | Weight (g) |
| Trimethylsilyl terminated polydimethysiloxane | Gelest DMS T72 | 120 |
| dimethylvinyl silyl terminated polydimethysiloxane | Gelest DMS V52 | 120 |
| Example 1 | | 48 |
| Trimethylsilyl terminated polymethylhydrosiloxane | Gelest DMS HMS 991 | 2.4 |
| Triclosan | | 60 |
| Solvent 1 | Xylene | 510 |
| Solvent 2 | Heptane | 879 |

The above components were mixed together in a high shear mixer at a speed of 30 Hz for 4 hours.

Example 2b—Coating of Test Articles

The following list of test articles were immersed into the solution of Example 2a for 5 seconds and cured at 100 C for 5 minutes.
 2b-1: Stainless Steel Suture: Ethicon Surgical steel suture M650G
 2b-2: Silicone Drain: Blake® silicone drains 2233
 2b-3: Titanium Pin: Synthes 2.0 mm Ti Kirschner wire 492.20 (only tested in *E coli*)
 Additionally, the treated test articles 2b-2 (Blake® silicone drain) and 2b-3 (Titanium Pin: Synthes 2.0 mm Ti Kirschner) were packaged in conventional Tyvex® bags and sterilized in ethylene oxide. These EO treated test articles were labeled 2b-2EO and 2b-3EO, respectively;
 2b-2EO: Silicone drain: Blake® silicone drains 2233
 2b-3EO: Titanium pin: Synthes 2.0 mm Ti Kirschner wire 492.20 (only tested in *E coli*)

Example 2c. Zone of Inhibition Tests

The above test articles were aseptically placed in individual sterile petri dishes and challenged with 100 micro liters of inoculum containing 10 colony-forming units (CFU) of *Staphylococcus aureus* or *Escherichia coli*. Trypticase soy agar (TSA) was poured into each dish and allowed to solidify. The plates were incubated at a temperature of 37

C for 24 hours. After incubation, the plates were examined under a darkfield colony counter and the Zones of Inhibition (ZOI) were measured. The results are summarized in Table 2c.

TABLE 2c

Zone of Inhibition (mm)

| Sample ID | Substrate | S. aureus | E. coli |
|---|---|---|---|
| 2b-1 | Stainless Steel suture | 10.8 | 4.5 |
| 2b-2 | Silicone drain | >40 | 17.4 |
| 2b-3 | Titanium pin | N/A* | 6.8 |
| 2b-2EO | Silicone drain | >40 | N/A* |
| 2b-3EO | Titanium pin | N/A* | 9.7 |

*N/A no test was done on these samples

Figure 2:
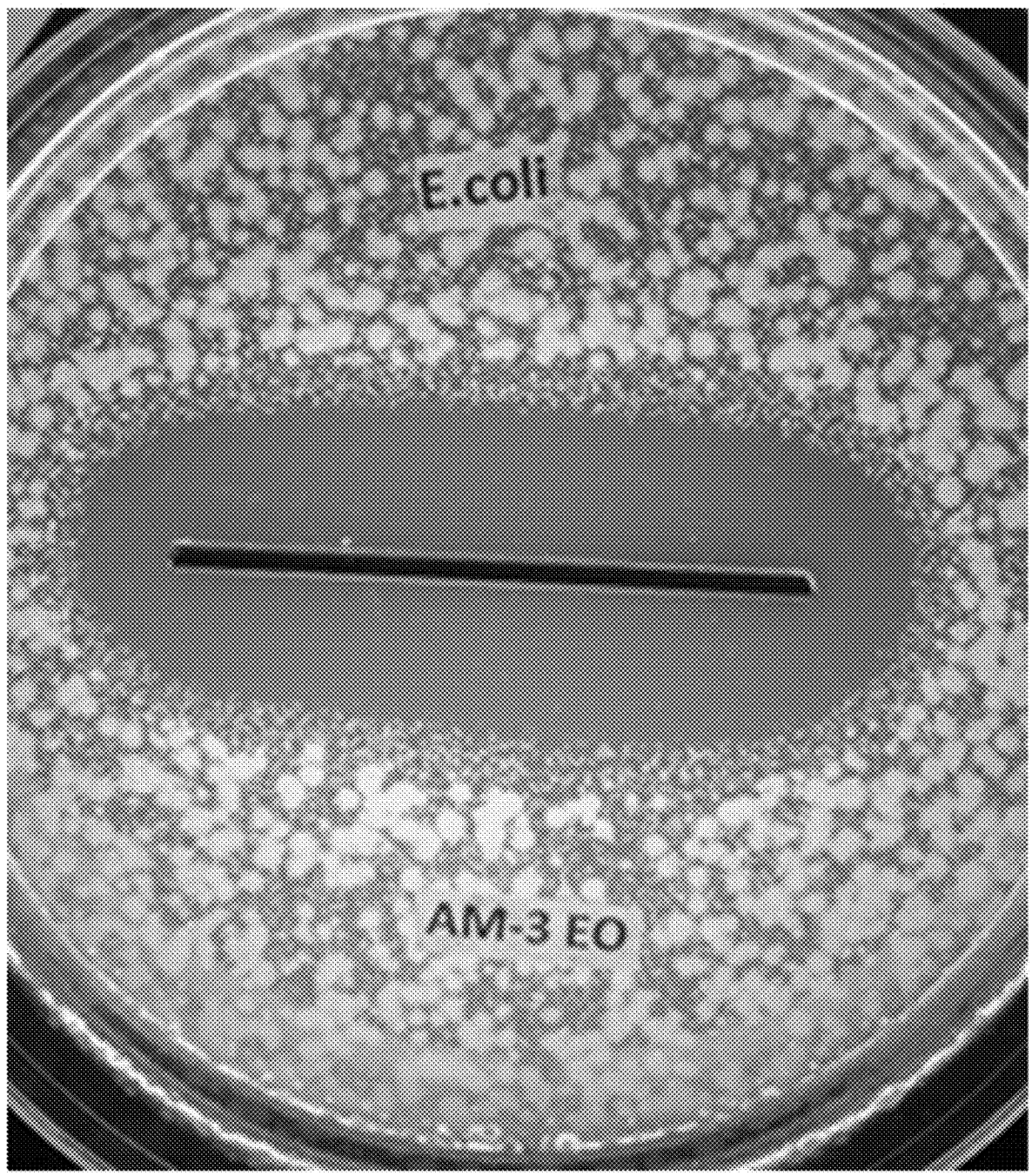
FIG. 2 is a Zone of Inhibition photo for one of the test articles coated with another embodiment of the novel antimicrobial coatings of this invention.

Referring to Table 2c, one sees that the coatings of this invention provide adequate zones of inhibition for the coated articles, with a 3 mm ZOI typically being accepted as a minimum effective ZOI. Further depiction of the effectiveness of the coatings of this invention can be seen in FIGS. 1 and 2. Referring to FIG. 1, the ZOI for Sample 2b-3 (titanium pin) is depicted while FIG. 2 depicts the ZOI for Sample 2b-3EO (titanium pin after EO sterilization on a TSA plate challenged with *E coli*. Further, as can be appreciated from FIG. 2, the antimicrobial compositions in the silicone compositions of this invention remain effective even after EO sterilization.

Example 3a, Preparation of a Coating Solution Leads to a 10 wt. % Triclosan-Containing Silicone This example provides a triclosan-containing silicone coating solution with a mixture of the components summarized in Table 3a.

TABLE 3a

Coating Formulation

| Component | Trade Name | Weight (g) |
|---|---|---|
| Trimethylsilyl terminated polydimethysiloxane | Gelest DMS T72 | 120 |
| dimethylvinyl silyl terminated polydimethysiloxane | Gelest DMS V52 | 120 |
| Example 1 | | 48 |
| Trimethylsilyl terminated polymethylhydrosiloxane | Gelest DMS HMS 991 | 2.4 |
| Triclosan | | 26.7 |
| Solvent 1 | Xylene | 510 |
| Solvent 2 | Heptane | 879 |

The above components were mixed together in a high shear mixer at a speed of 30 Hz for 4 hours.

Example 3b, Coating of Test Articles

The test articles were immersed into the solution of Example 2a for 5 seconds and cured at a temperature of 100 C for 5 minutes.
- 3b-1: Stainless steel suture: Ethicon Surgical steel suture M650G
- 3b-2: Silicone drain: Blake® silicone drains 2233

Additionally, the treated test article 3b-2 (Blake® silicone drain) was packaged in conventional Tyvex® bags and sterilized in ethylene oxide. This EO treated test article was labeled 3b-2EO.
- 3b-2EO: Silicone drain: Blake® silicone drains 2233.

Example 3c. Zone of Inhibition Test

The test articles of Example 3b were aseptically placed in individual sterile petri dishes and challenged with 100 micro liters of inoculum containing 10 colony-forming units (CFU) of *Staphylococcus aureus* or *Escherichia coli*. Trypticase soy agar (TSA) was poured into each dish and allowed to solidify. The plates were incubated at a temperature of 37 C for 24 hours. After incubation, the plates were examined under a darkfield colony counter and the Zone of Inhibition (ZOI) were measured. The results are summarized in Table 3c.

TABLE 3c

Zone of Inhibition (mm)

| Sample ID | Substrate | S. aureus | E. coli |
|---|---|---|---|
| 3b-1 | stainless steel suture | N/A* | 6.4 |
| 3b-2 | Silicone drain | N/A* | 11.1 |
| 3b-2EO | Silicone drain | >40 | 9.5 |

N/A* no test was done on this sample

Example 4a—Preparation of Coating Solution Leads to 5% Triclosan-Containing Silicone This example provides a triclosan-containing silicone coating solution with a mixture of the components summarized in Table 4a.

TABLE 4a

Coating Formulation

| Component | Trade Name | Weight (g) |
|---|---|---|
| Trimethylsilyl terminated polydimethysiloxane | Gelest DMS T72 | 120 |
| dimethylvinyl silyl terminated polydimethysiloxane | Gelest DMS V52 | 120 |
| Example 1 | | 48 |
| Trimethylsilyl terminated polymethylhydrosiloxane | Gelest DMS HMS 991 | 2.4 |
| Triclosan | | 12.6 |
| Solvent 1 | Xylene | 510 |
| Solvent 2 | Heptane | 879 |

The above components were mixed together in a high shear mixer at a speed of 30 Hz for 4 hours.

Example 4b—Coating of Test Articles

The following test articles were immersed into the solution of Example 2a for 5 seconds and cured at a temperature of 100 C for 5 minutes.
- 4b-1: Stainless steel suture: Ethicon surgical steel suture M650G
- 4b-2: Silicone drain: Blake® silicone drain 2233

Additionally, the treated test article 4b-2 (Blake® silicone drain) was packaged in conventional Tyvex® bags and sterilized in ethylene oxide. These EO treated test article was labeled 4b-2EO.
- 4b-2EO: Silicone drain: Blake® silicone drains 2233.

Example 4c—Zone of Inhibition Tests

The Example 4b test articles were aseptically placed in individual sterile petri dishes and challenged with 100 micro liters of inoculum containing 10 colony-forming units (CFU) of *Staphylococcus aureus* or *Escherichia coli*. Trypticase soy agar (TSA) was poured into each dish and allowed to solidify. The plates were incubated at a temperature of 37 C for 24 hours. After incubation, the plates were examined under a darkfield colony counter and the Zones of Inhibition (ZOI) were measured. The results are summarized in Table 4c.

TABLE 4c

| | Zone of Inhibition (mm) | | |
|---|---|---|---|
| Sample ID | Substrate | S. aureus | E. coli |
| 4b-1 | stainless steel suture | N/A* | 1.5 |
| 4b-2 | Silicone drain | 2 | 11.5 |
| 4b-2EO | Silicone drain | >40 | 9.5 |

N/A* no test was done on this sample

Example 5a—Preparation of Suture Coating Solution Leads to a 10 wt. % Triclosan-Containing Silicone This example provides triclosan-containing silicone coating solution with a mixture of the components summarized in Table 5a.

5b-1: 2-0 Silk Suture
5b-2: 1 PET (Mersilene®) Suture)

Example 5c—Performance Testing

The suture test articles of Example 5b were aseptically placed in individual sterile petri dishes and challenged with 100 micro liters of inoculum containing 10 colony-forming units (CFU) of *Staphylococcus aureus*. Trypticase soy agar (TSA) was poured into each dish and allowed to solidify. The plates were incubated at a temperature of 37 C for 24 hours. After incubation, the plates were examined under a darkfield colony counter and the Zone of Inhibition (ZOI) were measured. The test articles were extracted from the petri dishes and aseptically placed in another sterile petri dishes and challenged with 100 micro liters of inoculum containing 10 colony-forming units (CFU) of *Staphylococcus aureus*. Trypticase soy agar (TSA) was poured into each dish and allowed to solidify. The plates were incubated at a temperature of 37 C for another 24 hours. After incubation, the plates were examined under a darkfield colony counter and the Zone of Inhibition (ZOI) were measured. Three replicates of each sample were used for each test articles and the results are summarized in Table 5c.

TABLE 5c

| | | Zone of Inhibition (mm) | | | | | | |
|---|---|---|---|---|---|---|---|---|
| | | S. aureus | | | | | | |
| | | Day 1 | | | | Day 2 | | |
| Sample ID | Substrate | end | middle | end | Ave | end | middle | end | Ave |
| 5b-1 | 2-0 Silk | 7.5 | 7.8 | 7.4 | 7.6 | 2.3 | 2.7 | 2.4 | 2.5 |
| 5b-2 | 1 Mersilene | 9.8 | 11.2 | 10.7 | 10.6 | 6.0 | 6.3 | 5.8 | 6.0 |

TABLE 5a

| | Coating Formulation | |
|---|---|---|
| Component | Trade Name | Weight (g) |
| Liquid Silicone base rubber (silicone reinforced dimethylvinyl silyl terminated polydimenthylsiloxane) | Bluestart LSR4370 base | 570 |
| Example 1 | | 100 |
| Trimethylsilyl terminated polymethylhydrosiloxane | Gelest DMS HMS 991 | 17 |
| Triclosan | | 63.3 |
| Solvent 1 | hexamethyldisiloxane | 1040 |
| Solvent 2 | Heptane | 6160 |

The above components were mixed together in a high shear mixer at a speed of 30 Hz for 4 hours.

Example 5b—Coating of Test Articles 1 meter of Silk suture (Ethicon 2-0 Mersilene) was immersed into the coating formulation of Example 5a for 5 seconds and cured at a temperature of 100 C for 5 minutes.

200 meters of size 1 Mersilene® suture was immersed into the coating formulation of Example 5a and cured at a temperature of 100 C for 100 seconds through an in-line heating oven.

Referring to Table 5c, one sees the ZOI of the sutures measured at the ends of each suture and in the middle of each suture over a 2-day period.

Example 6a—Preparation of Triclosan-Containing Two-Part Coating Solutions

This example is for the preparation of thicker coatings for higher loadings of triclosan in a limited space to create a triclosan reservoir.

The mixture of the components for Part A of the composite is summarized in Table 6a-1.

TABLE 6a-1

| Part A Coating Formulation | | |
|---|---|---|
| Component | Trade Name | Weight (g) |
| Liquid Silicone base rubber (silicone reinforced dimethylvinyl silyl terminated polydimenthylsiloxane) | Bluestart LSR4370 base | 72 |
| Example 1 | | 0.2 |
| Solvent | Heptane | 27.8 |

The above Part A components were mixed together in a high shear mixer at a speed of 30 Hz for 4 hours.

The mixture of the components of Part B is summarized in Table 6a-2.

TABLE 6a-2

Part B Coating Formulation

| Component | Trade Name | Weight (g) |
|---|---|---|
| dimethylvinyl silyl terminated polydimethysiloxane | Gelest DMS V52 | 57.6 |
| Trimethylsilyl terminated polymethylhydrosiloxane | Gelest DMS HMS 991 | 2.3 |
| Triclosan | | 14.4 |
| Solvent | Heptane | 25.7 |

The above Part B components were mixed together in a high shear mixer at a speed of 30 Hz for 4 hours.

The components Part A and Part B were mixed by hand for 2 minutes prior to brushing onto the surface of a PET/aluminum laminate. The coated laminate was dried at ambient temperature for 12 hours prior to cured in an oven at a temperature of 100 C for 30 minutes. A 0.2 mm thick triclosan containing silicone coating was formed on a PET/aluminum laminate with 9×18 inch dimension. The total weight of the coating on this substrate was 23 g, and 2.3 g of triclosan was loaded onto this two-layer laminate.

Example 6b—Performance Testing

Figure 3:
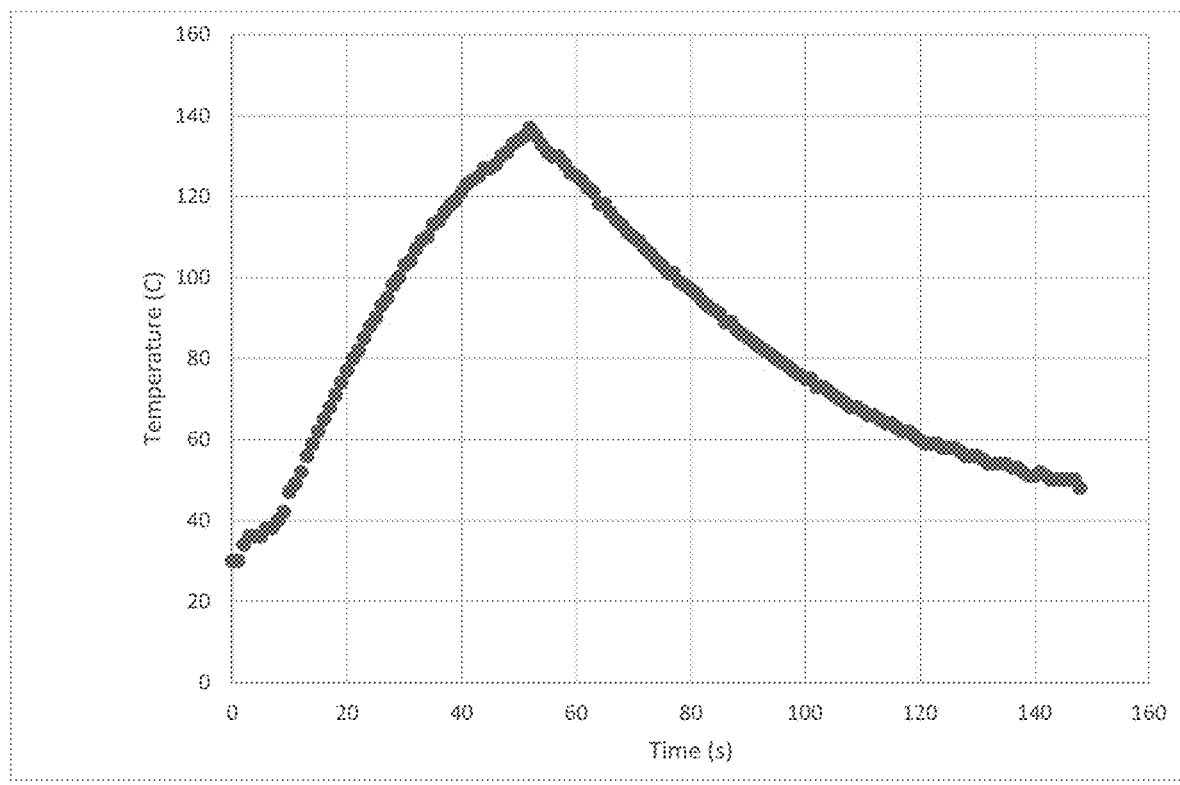
Figure 4:
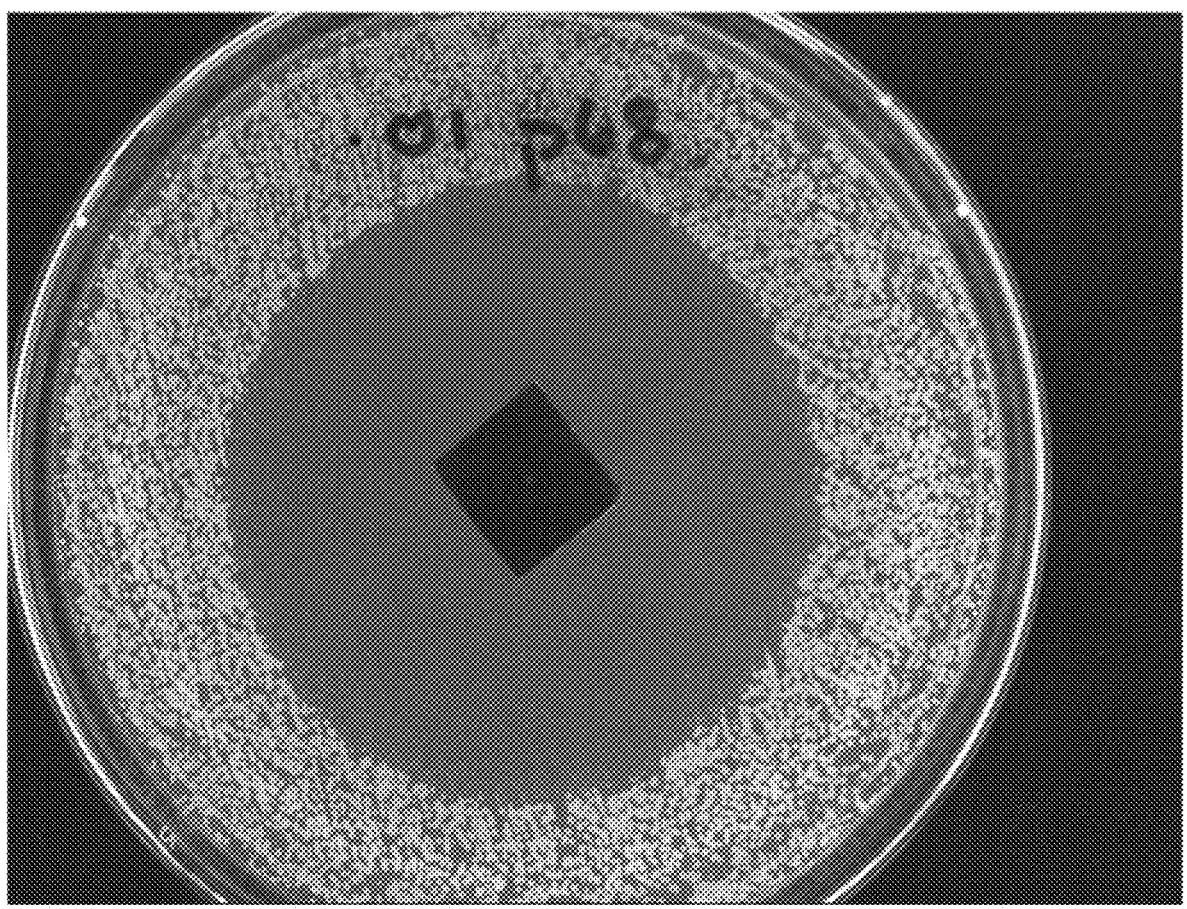
FIG. 4 is a Zone of Inhibition photo for one of the test articles treated with another embodiment of the novel antimicrobial coatings of this invention.

The coated laminate of Example 6a was used as triclosan reservoir for antimicrobially treating a ½" polished 316 stainless steel coupon as a test article. In practice the test coupon was placed in a closed container with the triclosan coated laminate of Example 6a and the contents of the container heated according to the heating profile depicted in FIG. 3 under a moderate vacuum of approximately—20 inches of mercury. The triclosan from the laminate of Example 6a transferred onto the surface of the stainless steel test coupon by the end of the heating cycle. The treated stainless steel coupon was then incubated at a temperature of 38 C for 24 hours in an agar plate containing an initial *Staphylococcus aureus* inoculum of $10^5$ bacteria per cubic centimeter of solution. FIG. 4 indicates that a protective zone of inhibition of approximately 20 mm was formed around the treated test coupon indicating that the triclosan of the coated laminate of Example 6a was successfully transferred to the 316 stainless steel test coupon during the heating cycle.

Referring to the above illustrated examples, the triclosan-containing silicone compositions of this invention provides an effective means to deliver the antimicrobial onto the surface on a range of medical devices, especially those surfaces that typically non absorbable surface such as various type of metals. Silicone is a polymer with high permeation which possesses control release characteristics, as demonstrated in the multiple day zone of inhibition of triclosan containing silicone coated PET and silk suture. Triclosan can be stored into silicone matrix and released as needed under certain conditions.

The novel coatings and catalyst of the present invention have many advantages compared with the coatings and catalysts of the prior art. The coatings allow for precise control over the cross-linked polymer network structure, leading to consistency of the resulting coatings and the consistency of the performance of coated devices. The coatings provide a unique polymeric network structure, which provides both lubricity and durability of the resulting silicone coating. The catalyst provides command cured catalytic action, enabling the coating solution to form a film rapidly while possessing desirably long pot life. The catalyst is inhibited at low or ambient temperatures and uninhibited or reactivated at temperatures that do not deform polymeric sutures or other polymeric medical devices or do not denigrate the effectiveness of the antimicrobial agents. The coatings and catalysts provide for more efficient coating and curing processes.

Although this invention has been shown and described with respect to detailed embodiments thereof, it will be understood by those skilled in the art that various changes in form and detail thereof may be made without departing from the spirit and scope of the claimed invention.

We claim:

1. A medical device coated with a lubricious silicone coating, comprising:
   a medical device having a surface; and,
   a lubricious silicone coating on at least a part of the surface, the coating formed from a coating composition comprising:
      a cross-linkable silicone polymer having reactive functionalities;
      optionally, a silica-containing composition;
      a silicone cross-linking agent;
      an antimicrobial agent selected from the group consisting of triclosan, chlorhexidine, polyhexamethylene biguanide (PHMB), octenidine, and silver; and,
      a catalyst, wherein said catalyst consists essentially of platinum divinyltetramethyldisiloxane vinylcyclohexanol complex having the formula:

$Pt[(CH_2=CH)(CH_3)_2Si]_2O \cdot C_6H_{10}(OH)(C=CH)$.

2. The medical device of claim 1, wherein the cross-linkable silicone polymer is selected from the group consisting of vinyl terminated polydialkylsiloxane, vinyl terminated polydimethylsiloxane, vinyl terminated polydiphenylsilane-dimethylsiloxane copolymer, vinyl terminated polyphenylmethylsiloxane, vinyl terminated polyfluoropropylmethyl-dimethylsiloxane copolymer and vinyl terminated polydiethylsiloxane.

3. The medical device of claim 1, wherein the cross-linkable silicone polymer comprises vinyl terminated polydimethylsiloxane.

4. The medical device of claim 1, wherein the antimicrobial agent is triclosan.

5. The medical device of claim 1, wherein the silicone cross-linking agent is selected from the group consisting of polymethylhydrosiloxane, polymethylhydro-co-polydimethylsiloxane, polyethylhydrosiloxane, polymethylhydrosiloxane-co-octylmethylsiloxane, and polymethylhydrosiloxane-co-methylphenylsiloxane.

6. The medical device of claim 1, wherein the silicone cross-linking agent comprises polymethylhydrosiloxane.

7. The medical device of claim 1, wherein the silica-containing composition comprises a trimethyl silyl surface treated silica filler.

8. The medical device of claim 1, wherein the silica-containing composition is selected from the commercially available reactive silica-containing silicone bases including HCR (high consistent rubber) bases and LSR (liquid silicone rubber) bases.

9. The medical device of claim 8, wherein the silica-containing composition is a liquid silicone rubber base.

10. The medical device of claim 1, wherein the coating composition additionally comprises about 20 wt. % to about 99.5 wt. % of an organic solvent, based upon the weight of the coating composition.

11. The medical device of claim 1, wherein the coating solution comprises about 1 to 40 wt. % (total solids) of triclosan antimicrobial agent.

12. The medical device of claim 1, wherein the coating composition comprises about 0.2 wt. % to about 1.8 wt. % of the silicone cross-linking agent based on total solids, wherein the coating composition additionally comprises about 75 wt. % to about 99.5 wt. % of an organic solvent, based upon the weight of the coating composition.

13. The medical device of claim 1, wherein the coating composition comprises about 0.0004 wt. % to about 0.0036 wt. % of the platinum catalyst, based on total solids, wherein the coating composition additionally comprises about 75 wt. % to about 99.5 wt. % of an organic solvent, based upon the weight of the coating composition.

14. The medical device of claim 1, wherein the coating composition additionally comprises a solvent selected from the group consisting of xylene, toluene, pentane, hexane, heptanes, octane, mixtures of higher molecular weight olefins, and combinations thereof.

15. The medical device of claim 1, wherein the medical device comprises a biocompatible material selected from the group consisting of stainless steels, PTFE, glasses, ceramics, polymers, refractory metal alloys, memory alloys, and composites of metals and non-metals.

16. The medical device of claim 1, wherein the medical device is selected from the group consisting of surgical needles, sutures, hypodermic needles, surgical scalpels, catheters, cutting blades, surgical probes, endoscopes, scissors, and cutting blades.

17. The medical device of claim 16, wherein the medical device comprises a surgical suture.

18. The medical device of claim 1, wherein the coating further comprises a non-cross-linkable siloxane.

19. The medical device of claim 18, wherein the non-cross-linkable siloxane is trimethylsilyl-terminated polydimethylsiloxane.

20. A coating composition comprising:
a cross-linkable silicone polymer having reactive functionalities;
optionally a silica-containing composition;
optionally a non-cross-linkable siloxane;
a silicone cross-linking agent;
an antimicrobial agent selected from the group consisting of triclosan, chlorhexidine, polyhexamethylene biguanide (PHMB), octenidine, and silver; and
a catalyst, wherein said catalyst consists essentially of platinum divinyltetramethyldisiloxane vinylcyclohexanol complex having the formula:

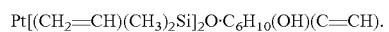

21. The coating composition of claim 20, wherein the composition is curable at temperatures above about 70 C.

22. The coating composition of claim 21, wherein the composition is curable at temperatures of about 95 C in about 2 minutes.

* * * * *